United States Patent [19]

Deamer et al.

[11] Patent Number: 4,829,989
[45] Date of Patent: May 16, 1989

[54] STOOP LABORER'S BODY SUPPORT HAVING HINGE WITH ADJUSTABLE SPRING BIASING

[76] Inventors: Richard M. Deamer, 768 Via Cielito, Ventura, Calif. 93003; David W. Deamer, 2740 Rubicon, Davis, Calif. 95616

[21] Appl. No.: 35,370

[22] Filed: Apr. 7, 1987

Related U.S. Application Data

[63] Continuation-in-part of Ser. No. 744,939, Jun. 17, 1985, abandoned.

[51] Int. Cl.$^4$ ................................................ A61F 5/02
[52] U.S. Cl. ...................................... 128/78; 128/80 F
[58] Field of Search ................... 128/78, 75, 781, 804, 128/80 F, 80 G, 88; 2/44

[56] References Cited

U.S. PATENT DOCUMENTS

| | | | |
|---|---|---|---|
| 443,113 | 12/1890 | Ray | 2/44 |
| 703,477 | 7/1902 | Russell | 2/44 |
| 888,490 | 5/1900 | Haas | 128/78 |
| 911,243 | 2/1909 | Johannesen | 128/80 F |
| 1,191,769 | 7/1916 | Curts et al. | 2/44 |
| 1,641,027 | 8/1927 | Feaster | 2/44 |
| 1,939,097 | 12/1933 | Bauman | 128/80 F |
| 4,397,308 | 8/1983 | Hepbam | 128/88 |
| 4,481,941 | 11/1904 | Rolfes | 128/88 |

FOREIGN PATENT DOCUMENTS

| | | | |
|---|---|---|---|
| 37574 | 2/1956 | Poland | 128/78 |
| 2056860 | 3/1981 | United Kingdom | 128/78 |
| 2098490 | 11/1982 | United Kingdom | 128/78 |

OTHER PUBLICATIONS

Copy of translation of Polish patent 37574 included.

Primary Examiner—David Wiecking
Assistant Examiner—Tonya Lamb
Attorney, Agent, or Firm—Marvin E. Jacobs

[57] ABSTRACT

A portable spring leveraged device adapted for attachment to the hips in a manner that allows a person engaged in so-called "stoop labor" to bend or flex at the hips with less physical exertion, and with less stress and strain on involved musculature and vertebral joints. The device consists of a U-shaped metal or plastic frame, hinged in each arm of the U and provided with spring resistance at each hinge point. The frame is belt-mounted at the wearer's waist with the hinge points adjacent the hips and with the bottom of the U and arms providing padded contact at the wearer's chest and thighs, respectively. The two arms provide for independent leg movement for walking while the chest contact resiliently supports a major portion of the wearer's upper torso weight during leaning and stooping, thus relieving the stresses and strains normally imparted to the back muscles, ligamentous and bony support, and especially the low back structure, during, for example, use of a short hoe and/or lifting produce boxes.

18 Claims, 3 Drawing Sheets

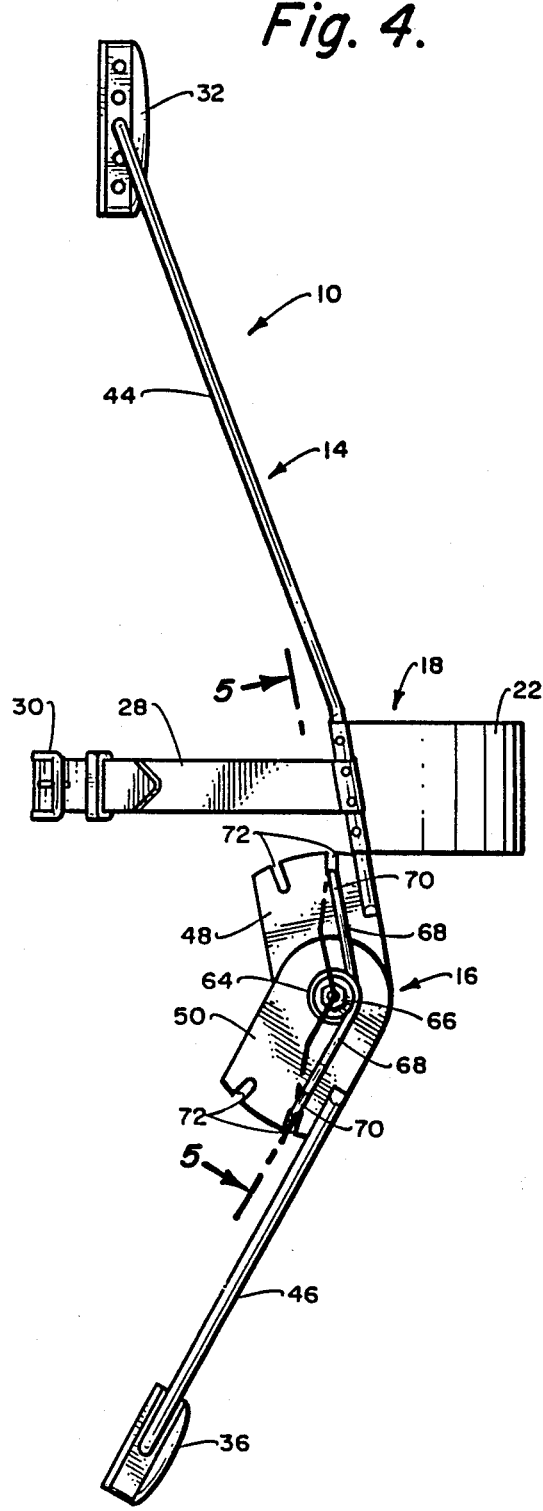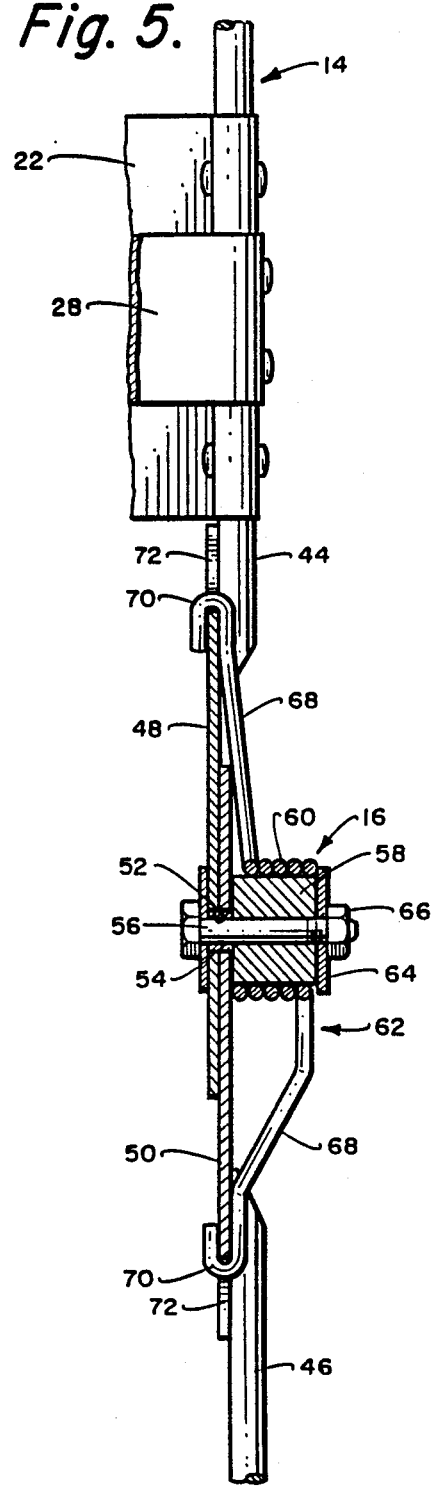

STOOP LABORER'S BODY SUPPORT HAVING HINGE WITH ADJUSTABLE SPRING BIASING

CROSS-REFERENCE TO RELATED APPLICATION

This application is a continuation-in-part of copending application Ser. No. 744,939, filed June 17, 1985 now abandoned.

TECHNICAL FIELD

The present invention relates to devices for providing support to portions of the human body and, more particularly, to a body support for relieving stress and strain on the back during bending at the waist.

Many agricultural operations are best performed by so-called "stoop labor", that is, individual laborer bending and stooping to employ hand-held farm implements such as rakes, produce boxes, hoes, and the like in thinning, weeding, planting and harvesting operations. Continued bending at the waist can be particularly tiring on and potentially damaging to the involved musculature and vertebral joints. For example, it has been documented that the use of a short hoe in the stooped position is especially damaging to low back structure.

What has been needed for a long time is a device which will simply and inexpensively provide support for the worker's upper torso during the bending and stooping operations while, at the same time, providing freedom and ease of movement both during the bending and stooping operations as well as in general movement and walking.

| List of Prior Art | |
|---|---|
| Patent No. | Patentee |
| 888,490 | G. W. Haas |
| 911,243 | K. Johannsen |
| 1,544,162 | A. J. LaVigne |
| 1,939,097 | A. W. Bauman |
| 3,543,748 | J. D. Charters |
| 3,993,056 | P. Rabischong, et al |
| 4,169,467 | P. Rabischong, et al |
| 4,349,195 | M. Johnston |
| 4,397,308 | G. R. Hepburn |
| 4,481,941 | T. A. Rolfes |
| 479.873 | French (Robin) |
| 37,574 | Poland (Gadewski) |
| 2,056,860 | Great Britain (Witchell) |

Many orthopedic devices have been devised to firmly support the body of a patient to immobilize or support a traumatic joint area.

The French Patent discloses a therapy device having two U-shaped members joined at a set of opposed spring board pivots. The device can include a belt as shown in FIG. 3. However, this device is designed for support of knees, arms, neck, legs or shoulders and not as a back support and does not utilize two independently articulated members.

The other references individually show various elements of a device used in orthopedic supports such as chest pads, knee pads, hinges and belts.

The Haas brace includes back and front portions joined by a belt. Each portion contains a lower plate and upper shoulder frame joined by a flexible member. LaVigne's back brace is a harness-type device including elongated coil springs. The harness shown by Charters has resilient side members. Rabischong et al use inflatable sleeves articulated at positions corresponding to body joints. Johnston discloses a standing support having a chest pad. Rolfes illustrates a hip stabilizer having a waist belt and a thigh belt connected by a hinge brace 22.

In the Bauman body brace, the hip joint and knee joint are constrained to move around centers of rotation which do not duplicate natural movement. Natural movement takes place through locus of centers. So the mechanical structure of this prothesis is imposing, rather than relieving, strain on the involved joint. Constraint between members 23b, 24, 25 and 26 would severely interfere with the free movement required during gardening or farming. In fact, the multiplicity of clamps and straps throughout the full length of the support structure is a classical example of problem discussed above. Spring 20 at the knee joint imposes a straightening force on the knee that is inconsistent with the free knee bending required of a stooped laborer.

Obviously, severe problems of knee joint constraint are also present in the Johannsen prothesis. The configuration of members described in the claims of this patent do not accomplish the objective stated in lines 10 through 15. The reactive forces across the pivot stud 19 generate a torque around the patient's leg when he walks. One would expect that forms 11 and 15 would need a firm, even tight, fit on the leg to prevent instability of the attached arms. It is believed that this condition would introduce forces leading to additional injury rather than benign, healing support of the joint. Moreover, the cam cluster 16, 17, 18, 19 cannot be adjusted without displacing the bars 12 and 5 forward or backward from the position shown in FIG. 1. It appears that this would introduce a lateral force on the knee joint, and lead to further injury.

In contrast to Bauman and Johannsen, Hepburn does recognize the torque problem on the patient's leg discussed above. Torque reaction is avoided by utilizing a set of clamped rods on both sides of the limb. Again, the user is severely constrained. Some method of duplicating the instant-center locus of joint rotation must be provided by this equipment instead of a simple rotary joint. The off-center contact between cam surface 10 and nose element 24 will result in mechanical lock-up.

The long extensions 2 and 3 are made part of the spring in Witchell. This introduces additional flexible spring material that lowers the spring force below that necessary to counterbalance the forces introduced by the body in stooping or in bending. No position stops are shown on the harness. The exposed location of this spring subjects the wearer to injury from flying parts in case of breakage under load.

The Gadewski prosthetic device is utilized as a brace to straighten the back and support the chin. As such it has little relationship to stoop labor body support. No thigh reaction is involved and the hinge shown in FIG. 4 is placed well above the center of hip rotation location. The spring depicted is obviously unguarded and in failure would be in a position to injure the patient.

Many of these prior devices are not useful for their intended purpose and ae particularly not useful or adaptable for use as a stoop labor support. They do not (1) firmly support the body of the user in a kneeling or stooped position; (2) applying a counteracting resisting force to the body matching the bending force on the device during bending; (3) avoid constraint of arm and leg limbs and (4) provide freedom to walk. Several of these devices are bulky and excessively heavy for carrying on a working laborer. The prior orthopedic devices can be heavy since they are designed to immobilize the user. The stoop labor support of the invention is designed to promote movement for efficiency in use of arm and hand by a working laborer in a stooped or kneeling position.

STATEMENT OF THE INVENTION

The present invention provides a device whereby stoop laborers no longer have their upper torso solely supported by back muscle, ligament and tendom tissue. The individual equipped with the body support device of the invention no longer need place the delicate balance of the tissue in his/her low back at risk of sprain and strain, thereby allowing the use of the short hoe, and like farm implements, again without the damaging consequences.

The body support of the present invention for relieving stress and strain on the back during bending at the waist comprises a generally U-shaped frame having a cross-piece connecting two arms which are resiliently flexible about respective hingepoints; and, means for supporting the frame on a wearer's torso with the cross-piece positioned to bear against the wearer's chest, the ends of the arms positioned to independently bear against the anterior surface of respective ones of the wearer's legs intermediate the hips and knees, and the hingepoints juxtaposed at each of the wearer's hips approximately on a centerline through the hip joints, whereby as the wearer bends at the hip, a portion of the upper torso weight is resiliently supported.

In the preferred embodiment, the arms each include respective ones of a pair of springs each including a hinge at respective ones of the hingepoints for providing an adjustable reactive force about the hinge as the wearer bends the arms at the hinge by bending at the hip. Additionally, force adjustment means are provided connecting the springs to the arms for adjusting the amount of the reactive force. Also, positional adjustment means are provided connecting the springs to the arms for selecting an initial point in the wearer's bending at the hip at which the body support begins to provide the resilient support.

To provide additional benefits in the preferred embodiment, stop means are operably connected to the arms adjacent respective ones of the hinges for selecting a final point in the wearer's bending at the hip at which the body support stops pivoting about the hinge and acts as a platform to totally transfer the upper torso weight to the wearer's legs. The stop means are also adjustable, whereby the final point can be selectively set by the wearer.

The support of the invention does not interfere with the laborer as he bends, picks, hoes or harvests. These operations require free use of the arms and legs. The arms must be free to handle tools and to work in an area surrounding the laborer as he stoops or kneels or bends his body. The legs must also not be constrained as the laborer changes position to move further down a row or to move from a kneeling or bending position to a straight position. In every work position, the pads apply a counteracting force to support the body.

Since the support device of the invention is used outdoors in the hot sun, the pads are preferably formed of absorbent material and are removable from the pad packing member. The pads camn be formed of disposable or washable material. The device of the invention is designed to provide no support when the body is in an upright position. The device fits loosely and both pads do not apply any force to the chest or thighs of the laborer. He can freely walk about with the lightweight device carrier by the waist belt. As soon as he starts to bend, the pads will resist bending and apply a support force through the spring.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 4 is a side elevation view of the body support of the present invention as viewed from the plane 4—4 in FIG. 3;

FIG. 5 is a cutaway enlarged view of the body support of the present invention as viewed in the plane 5—5 in FIG. 4.

DETAILED DESCRIPTION OF THE INVENTION

Figure 1:
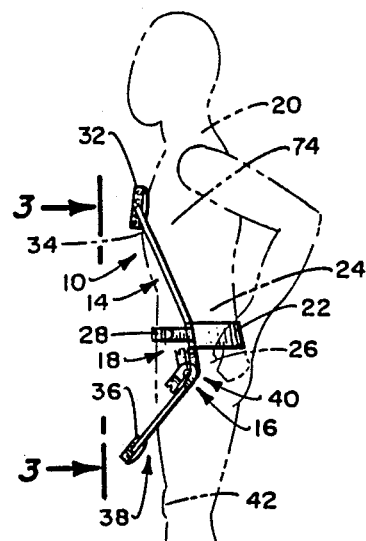
FIG. 1 is a side view of a person wearing the body upport of the present invention while standing erect.
Figure 2:
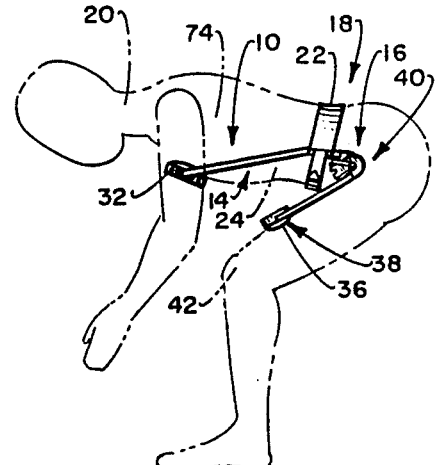
FIG. 2 is a side view of a person wearing the body support of the present invention while bending and stooping.
Figure 3:
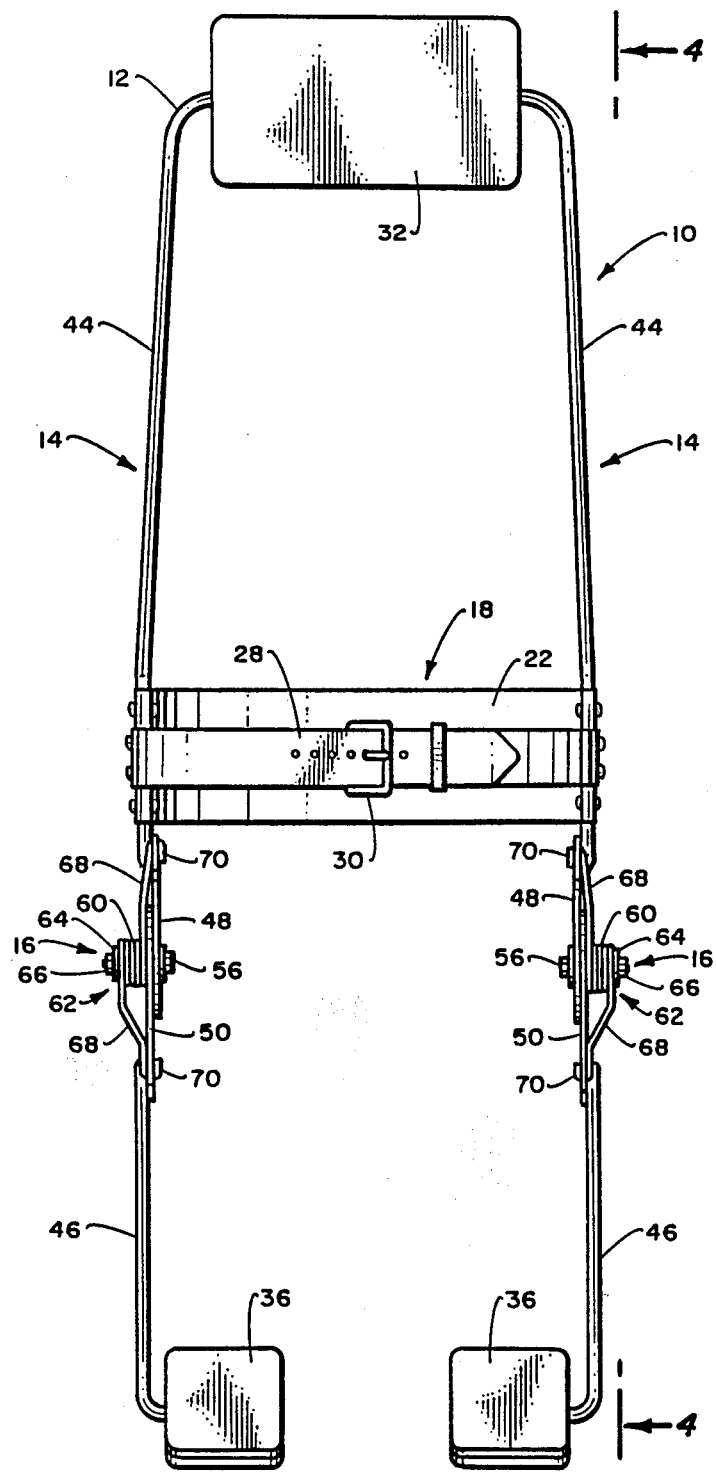
FIG. 3 is a front elevation view of the body support of the present invention as viewed from the plane 3—3 in FIG. 1.

With particular reference initially to FIGS. 1 and 3, the body support of the present invention comprises a generally U-shaped frame 10 having a cross-piece 12 and a pair of arms 14 each containing a resiliently flexible hinge point, generally indicated as 16. The frame 10 can be of metal or other structural material. The frame 10 has a releasable supporting and positioning member 18 for supporting the frame 10 on the torso of a wearer, such as that indicated in ghosted form at 20 in FIGS. 1 and 2. The supporting and positioning member 18 includes a wide positioning member 22 of plastic, or the like, connected between the two arms 14 and adapted to contact the wearer's waist 24 and ride on the wearer's upper hips at 26 to repeatably position the frame 10 on the wearer 20 in a manner to be described shortly. The supporting and positioning member 18 also includes a belt 28 connected between the arms 14 and including a buckle 30 for releasing and adjusting the belt 28.

Figure 6:
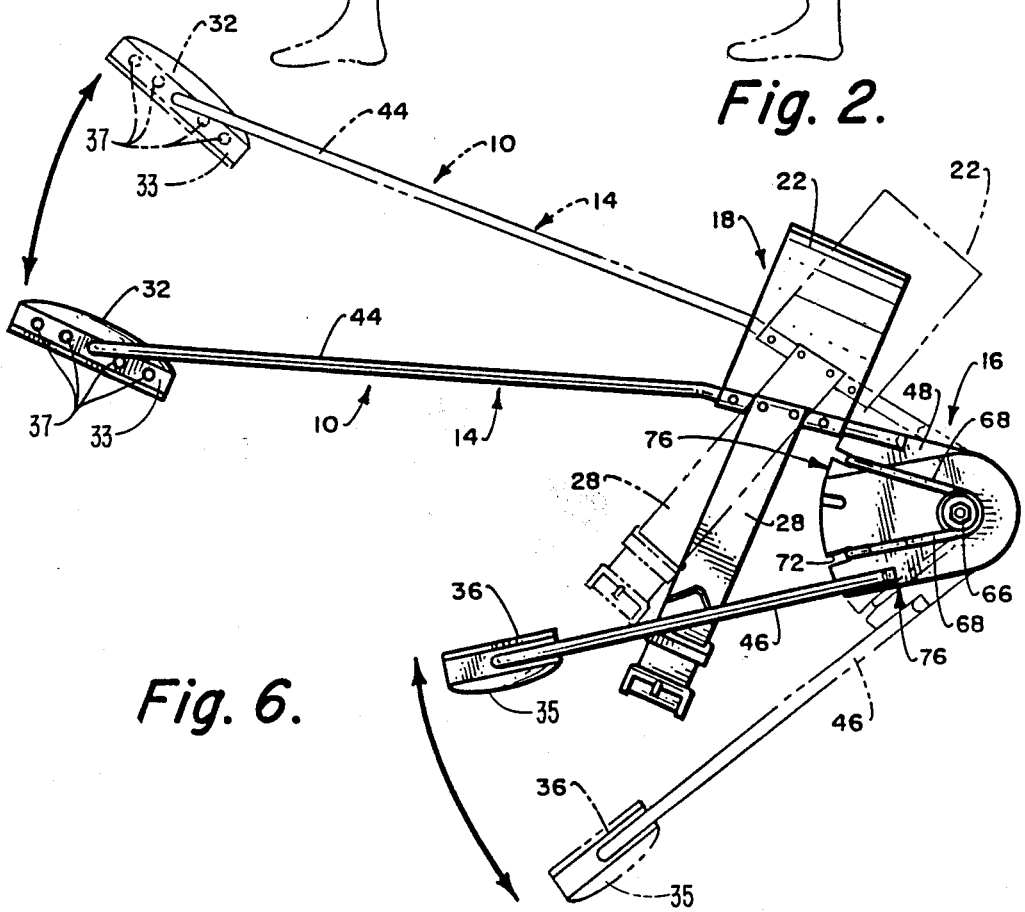
FIG. 6 is a side elevation view of the body support of the preent invention showing the flexing and support action thereof.

As shown in FIG. 6, the cross-piece 12 has a wide pad 32 received in a holder 33 which is pivotally mounted thereon for contact with the wearer's chest 34. The ends of the arms 14 each has a pad holder 36 pivotally mounted thereon for contact with the anterior portion of the wearer's upper leg at a position 38 between the hip joint at 40 and the knee 42. A resilient pad 35 is received in the pad holder 36. The pads 32, 35 are formed of resilient material such as foam, gauze or paper. The pads are also absorbent to absorb perspiration. The pads may be removable for washing by releasing screw fasteners 37 on the chest holder 32 or the Velcro backing on the thigh pads 35. In general, in order to provide proper freedom or movement, the position 38 (ghosted) has been found to be best with the pads 35 displaced from the knee 42 and the pad 32 lightly resting on the chest 34 of the laborer while the wearer 20 is standing as in FIG. 1. This allows sufficient freedom for a normal stride and transfers load only after the position shown in FIG. 2 is reached when stooping or bending.

Turning now primarily to FIGS. 4 and 5, the hinge point 16 will now be described in greater detail. In the preferred and tested embodiment as shown, each arm 14 includes an upper portion 44 and a lower portion 46. Each upper portion 44 terminates in a flat hinge plate 48 while each lower portion 46 terminates in a mating flat hinge plate 50. The hinge plates 48, 50 contain matching bores 52 into which a cylindrical spacer 54 of a length slightly longer than the thickness of the two plates 48, 50 is placed. A bolt 56 is passed outwardly through the bores 52. A cylindrical hub 58 is positioned over each of the bolts 56 and the helical center portion 60 of the spring member, generally indicated as 62, is positioned over the hub 58. The whole assembly is firmly held together by the large diameter washer 64 and nut 66. Because of the length of the spacer 54, even with the nut 56 tightened, the hinge plates 48, 50 are free to pivot about the outer surface of the spacer 54. To provide the proper pivoting action with respect to the wearer's natural bending points, the sizing and positioning of the supporting and positioning member 18 and the various parts hereinbefore described should be such as to place the bolt 56 approximately on a centerline through the ball socket of the hip joints of the wearer. The distance from belt 28 to the bolt 56 should approximate the distance from the top of the hips to the center of the hip joint of the user.

The spring 62 includes arms 68 extending radially outward from the helical center portion 60. Arms 68 have hooked ends 70 adapted to fit into notches 72 provided in the hinge plates 48, 50 for the purpose. As can be seen, a number of the notches 72 are provided in order to make provision for certain adjustments to be described shortly. As those skilled in the art will realize, numerous constructions are possible for the hinge points 16 so as to provide the flexing and resilient biasing forces to be described shortly, all within the scope and spirit of the invention being described herein.

As will be readily understood from FIGS. 4 and 6 and the following description, the hinges 16 provide many features of benefit in the body support of the present invention. For example, the choice of which notches 72 are used for the positioning of the hooked ends 70 in the notches 72 sets the initial biased angular relationship between the upper portions 44 and the lower portions 46 of the arms 14. The setting also determines the amount of force applied by the pads to the body of the user. This angular relationship acts as a positional adjustment means for selecting an initial point in the wearer's bending at the hip at which the body support begins to provide its resilient support; that is, the point at which, in the wearer's bending, the pad 32 begins to bear on the chest 34, the pads 35 begin to bear on the legs at 38, and the springs 62 begin to be twisted about the hub 58 and provide a reactive force to support the upper torso 74 of the wearer 20.

Additionally, the hooked ends 70 passing through the notches 72 prevent unlimited pivotal rotation of the hinge plates 48, 50 about the spacer 54. As shown in the non-ghosted position of FIG. 6, there comes a point as the wearer continues to bend over where the hooked ends 70 in the notches 72 jam against the edges of the hinge plates 48, 50 as at 76 and prevent further rotation. At that point, the body support acts as a platform with only the flexibility provided by the flexure potential of the arm portions 44, 46. Thus, the upper torso 74 is virtually completely supported and the weight thereof is transferred through the body support of the present invention to the wearer's legs. The selection of the notches 72 used, therefore, makes the above-described stopping point adjustable. If desired, separate stops in the form of, for example, bolts through holes provided therefor could be used to provide the stopping point.

Because of the adjustability features as described and the independent leg movement provided by the independently pivotal hinges 16, it can be appreciated that the body support of the present invention provides the ease of movement desired during walking and general movement as well as during the bending and stooping motions of the wearer.

It is to be realized that only preferred embodiments of the invention have been described and that numerous substitutions, modifications, and alterations are permissible without departing from the spirit and scope of the invention as defined in the following claims.

We claim:

1. A body support for relieving stress and strain on the back during bending at the waist comprising:
   (a) generally U-shaped frame having a pair of upper arms each with upper and lower ends, a pair of lower arms each with upper and lower ends, a cross-piece connected to and extending between said upper ends of said upper arms, and a pair of hinges each having a pair of parts rotatably connected together in a side-by-side relationship and correspondingly rigidly connected to said respective lower ends of said upper arms and upper ends of said lower arms for rotatably connecting said upper ends of said lower arms to said lower ends of said upper arms;
   (b) means for supporting said frame on a wearer's torso with said cross-piece positioned to bear against the wearer's chest, said lower ends of said lower arms positioned to bear against the anterior surface of respective ones of the wearer's legs intermediate the hips and knees, and said hinges being disposed at the opposite sides of the user approximately on a centerline through the hip socket, whereby as the wearer bends at the hip, a portion of the upper torso weight is resiliently supported; and
   (c) a pair of hinge biasing means separate from but mounted to said respective hinges adjacent to said respective parts thereof, said pair of hinge biasing means being coupled to said respective parts of said respective hinges such that said cross-piece and lower arms of the support do not support the body of the user in stand-up position but as the upper and lower arms rotate through bending said pair of hinge biasing means, via said parts of said hinges and said upper and lower arms rigidly connected to said respective hinge parts, will apply a counteracting support force to the chest and thighs of the user.

2. The body support of claim 1 wherein:
said supporting means comprises a releasable belt attached to said frame and includes positioning means for contacting the wearer's waist area to repeatably place said hinges in said position.

3. The body support of claim 1 and additionally comprising:

pads carried by said cross-piece and lower ends of said lower arms of said frame where said frame respectively contacts the wearer's chest and legs.

4. The body support according to claim 3 further including pad holders and means for releasing the pads from the holders.

5. The body support of claim 4 in which the pads are formed of resilient and absorbent material.

6. The body support of claim 1 wherein:
said pair of hinge biasing means respectively comprise a pair of springs being located adjacent said respective pair of hinges and operably coupled to said respective parts of said hinges to provide a reactive force about said hinge parts as the wearer bends at the hip and causes rotation of said upper and lower arms of said body support at said hinges via said respective rotatably connected hinge parts.

7. The body support of claim 6 and additionally comprising:
force adjustment means defined on said respective parts of said each of said hinges for coupling said springs to said respective hinge parts and being adapted for selectively adjusting the amount of said reactive force.

8. The body support of claim 7 wherein:
said force adjustment means are also adapted for selecting an initial point in the wearer's bending at the hip at which said body support begins to provide said resilient support.

9. The body support of claim 7 wherein:
said force adjustment means are also adapted for selecting a final point in the wearer's bending at the hip at which said body support stops pivoting about said hinges thereof and acts as a platform to totally transfer support of the upper torso weight to the wearer's legs.

10. The body support of claim 9 wherein:
said force adjustment means are adjustable whereby said final point can be selectively set by the wearer.

11. The body support of claim 7 wherein:
said springs each has hooked opposite ends; and
said force adjustment means defined on said hinge parts are in the form of spaced apart notches adapted to selectively receive said hooked ends of said springs for coupling said springs to said hinge parts and selectively adjusting the amount of said reactive force.

12. The body support of claim 11 wherein:
said biasing means also comprises a pair of hubs rotatably mounted to said respective pair of hinges adjacent to said rotatably connected hinge parts thereof, each of said springs being mounted to one of said hubs.

13. A body support for relieving stress and strain on the back during bending at the waist comprising:
(a) a generally U-shaped frame having a pair of upper arms each with upper and lower ends, a pair of lower arms each with upper and lower ends, a cross-piece connected to said upper ends of said upper arms, a pair of hinges each having a pair of hinge plates rotatably connected together in a side-by-side relationship and correspondingly rigidly connected to said respective lower ends of said upper arms and upper ends of said lower arms for rotatably connecting said upper ends of said lower arms to said lower ends of said upper arms, and a pair of springs being located adjacent said respective pair of hinges and operably coupled to said respective plates thereof for providing a reactive force about said hinge plates as the wearer bends at the hip and causes rotation of said upper and lower arms of said body support at said hinges via said respective rotatably connected hinge plates;

(b) a plurality of pads carried by said cross-piece and lower ends of said lower arms of said frame where said frame respectively contacts the wearer's chest and legs;

(c) means for supporting said frame on a wearer's torso with one of said pads carried on said cross-piece positioned to bear against the wearer's chest, other of said pads carried on said lower ends of said arms positioned to bear against the anterior surface of respective ones of the wearer's legs intermediate the hips and knees, and said hinges being juxtaposed at opposite sides of the wearer's hips approximately on a centerline through the hip joints, said supporting means comprising a releasable belt attached to said frame and including positioning means for contacting the wearer's waist area to repeatably place hinges in said juxtaposed positions, whereby as the wearer bends at the hip, a portion of the upper torso weight is resiliently supported; and (d) force adjustment means defined on said respective plates of said each of said hinges for coupling said springs to said respective hinge plates and being adapted for selectively adjusting the amount of reactive force.

14. The body support of claim 13 wherein:
said force adjustment means are also adapted for selecting an initial point in the wearer's bending at the hip at which said body support begins to provide said resilient support.

15. The body support of claim 13 wherein:
said springs each has hooked opposite ends; and
said force adjustment means defined on said hinge plates are in the form of spaced apart notches on the peripheries thereof adapted to selectively receive said hooked ends of said springs for coupling said springs to said hinge plates and selectively adjusting the amount of said reactive force.

16. The body support of claim 13 and additionally comprising:
a pair of hubs rotatably mounted to said respective pair of hinges adjacent to said rotatably connected hinge plates thereof, each of said springs being mounted to one of said hubs.

17. The body support of claim 13 wherein:
said force adjustment means are also adapted for selecting a final point in the wearer's bending at the hip at which said body support stops pivoting about said hinges thereof and acts as a platform to totally transfer the upper torso weight to the wearer's legs.

18. The body support of claim 17 wherein:
said force adjustment means are adjustable whereby said final point can be selectively set by the wearer.

* * * * *